United States Patent [19]
Engelson et al.

[11] Patent Number: 5,312,356
[45] Date of Patent: * May 17, 1994

[54] CATHETER WITH LOW-FRICTION DISTAL SEGMENT

[75] Inventors: Erik T. Engelson, Mountain View; Ivan Sepetka, Redwood City, both of Calif.

[73] Assignee: Target Therapeutics, Fremont, Calif.

[*] Notice: The portion of the term of this patent subsequent to Sep. 11, 2007 has been disclaimed.

[21] Appl. No.: 527,200

[22] Filed: May 22, 1990

Related U.S. Application Data

[63] Continuation-in-part of Ser. No. 355,500, May 22, 1989, Pat. No. 4,955,862.

[51] Int. Cl.⁵ ............... A61M 5/178; A61M 5/32; A61M 25/00
[52] U.S. Cl. ........................... 604/164; 604/265; 604/282
[58] Field of Search ............... 604/280-282, 604/164, 96-103, 264, 265; 128/656-658, 772, DIG. 14, DIG. 21; 606/192-194

[56] References Cited

U.S. PATENT DOCUMENTS

| | | | |
|---|---|---|---|
| 2,583,298 | 1/1952 | Kowan | 604/281 |
| 3,757,768 | 9/1973 | Kline | 128/657 |
| 4,219,520 | 8/1980 | Kline | 128/DIG. 21 |
| 4,368,730 | 1/1983 | Sharrock . | |
| 4,385,635 | 5/1983 | Ruiz | 128/658 |
| 4,597,755 | 7/1986 | Samson et al. | 604/96 |
| 4,636,346 | 1/1987 | Gold et al. . | |
| 4,676,229 | 6/1987 | Krasnicki et al. . | |
| 4,708,718 | 11/1987 | Daniels . | |
| 4,739,768 | 4/1988 | Engelson et al. . | |
| 4,784,639 | 11/1988 | Patel . | |
| 4,840,622 | 6/1989 | Hardy | 604/280 |
| 4,944,727 | 7/1990 | McCoy | 128/4 |
| 4,955,862 | 9/1990 | Sepetka | 604/282 |
| 4,976,703 | 12/1990 | Franetzki et al. | 604/265 |
| 5,037,404 | 8/1991 | Gold et al. | 604/282 |
| 5,047,045 | 9/1991 | Arney et al. | 606/194 |

FOREIGN PATENT DOCUMENTS

3034835 3/1982 Fed. Rep. of Germany ...... 604/282
3531 of 1913 United Kingdom .

Primary Examiner—C. Fred Rosenbaum
Assistant Examiner—Mark Bockelman
Attorney, Agent, or Firm—Morrison & Foerster

[57] ABSTRACT

A catheter for accessing a target site along a tortuous, small-vessel pathway. The catheter includes a flexible distal segment which is composed of a flexible polymer tube and a low-friction internal tubular surface. The surface allows the catheter to be advanced over sharp bends and small-diameter loops in a guidewire, in advancing the catheter along a small-vessel pathway. Various embodiments of the catheter are disclosed wherein the internal tubular surface of a distal portion of the catheter include a variety of different constructions and are comprised of a variety of different materials so as to best avoid the jamming, sticking or locking of the distal end or any part of the guidewire against the surface. Braided sleeve-like constructions, surfaces embedded with a plurality of small particles and surfaces comprised of various anti-friction materials are used in order to obtain the object of the invention.

15 Claims, 5 Drawing Sheets

CATHETER WITH LOW-FRICTION DISTAL SEGMENT

CROSS-REFERENCES

This Application is a continuation-in-part of co-pending U.S. application for "Catheter and Catheter/Guidewise Device," Ser. No. 355,500, filed May 22, 1989 now U.S. Pat. No. 4,955,862 which application is incorporated herein by reference and to which application is claimed priority under 35 USC §120.

FIELD OF THE INVENTION

The present invention relates to an improved catheter and catheter device for accessing a tissue target site along a tortuous or highly curved path through small vessels. More particularly, the invention relates to a catheter comprised of a tube and a guidewire wherein the internal surface of at least a portion of the tube is designed so as to facilitate the relative movement of the guidewire with respect to bent or curved portions of the tube and thus prevent jamming, sticking or locking of the guidewire against the internal tube surface.

BACKGROUND OF THE INVENTION

Catheters are being used increasingly as a means for delivering diagnostic or therapeutic agents to internal target sites that can be accessed through the circulatory system. For example, in angiography, catheters are designed to deliver a radio-opaque agent to a target site within a blood vessel, to allow radiographic viewing of the vessel and blood flow characteristics near the release site. For the treatment of localized disease, such as solid tumors, catheters allow a therapeutic agent to be delivered to the target site at a relatively high concentration with minimum overall side effects.

Often the target site which one wishes to access by catheter is buried within a soft tissue, such as brain or liver, and can only be reached by a tortuous route (i.e., a route including repeated sharp curves) through small vessels or ducts——less than about 3 mm lumen diameter——in the tissue. The difficulty in accessing such regions is that the catheter must be quite flexible in order to follow the tortuous path into the tissue, and at the same time, stiff enough to allow the distal end of the catheter to be manipulated from an external access site, which may be as much as a meter or more from the tissue site.

Heretofore, two general methods for accessing such tortuous-path regions have been devised. The first method employs a highly flexible catheter having an inflatable, but pre-punctured balloon at its distal end. In use, the balloon is partially inflated and carried by blood flow into the target site. The balloon is continually inflated during placement to replenish fluid leaking from the balloon. A major limitation of this method is that the catheter will travel in the path of highest blood flow rate, so many target sites with low blood flow rates cannot be accessed.

In the second method, a torqueable guidewire and catheter are directed as a unit from a body access site to a tissue region containing a target site. The guidewire is bent at its distal end and may be guided, by rotating and advancing the wire, along a tortuous, small-vessel pathway, to the target site. Typically the guidewire and catheter are advanced along the tortuous pathway by alternately advancing the wire along a region of the pathway, then advancing the catheter axially over the advanced wire portion. An important advantage of this method is the ability to control the location of the catheter along a tortuous path.

It is frequently desirable, for example, in treating deep brain vessel abnormalities, to direct a small-diameter catheter along a tortuous, small-diameter pathway to the brain vessel site. The procedure may be advisable, for example, in treating an arteriovenous malformation, in order to introduce an embolic agent into the small capillaries connecting the arterial and venous vessels at a deep brain site. At a certain point along the pathway, when sharp bends are first encountered, the catheter is advanced by alternately guiding the flexibletip portion of the guidewire along the path, then threading the catheter over a portion of the advanced wire region.

One problem which may be encountered, as the guidewire and catheter are advanced, is that the guidewire can become stuck against the internal tubular surface of the catheter. Typically, this problem arises when a sharp bend, such as a hairpin loop, is encountered and/or where two or more sharp bends occur in succession. When the catheter and wire become locked together (i.e., the end of the guidewire is jammed against the internal surface of the catheter tube so as to prevent the relative movement of the guidewire and internal tubular surface) in the region of wire bending, it may be impossible to either advance or withdraw the wire. In this event, the wire and catheter must be pulled back as a unit along the pathway until both are straight enough to allow the wire to be moved axially within the catheter, and often, the physician may have to give up attempting to reach the site.

The problem of advancing a catheter over a guidewire in a region of sharp wire bend(s) has been addressed by the catheter construction disclosed in U.S. Pat. No. 4,739,768. This construction includes a relatively long, relatively rigid proximal segment, and a shorter, more flexible distal segment having a length of at least about 5 cm. The proximal segment provides sufficient torqueability and axial stiffness for guiding the catheter and internal guidewire from a body access site to the target tissue of interest. Once the tortuous tissue pathway is reached, the more flexible end segment allows the end region of the catheter to be advanced axially over sharp and/or frequent wire bends.

SUMMARY OF THE INVENTION

A catheter device is disclosed which is comprised of two basic components including (1) an elongated guidewire having a proximal and a distal end; and (2) a catheter in the form of an elongated tubular member. The catheter or tubular member is comprised of two sections. The first section is toward the proximal end of the tubular member where, in a catheter device, it is connected to a proximal end fitting. The first section has substantially less flexibility relative to a second section which is toward a distal end of the tubular member. The second section is sufficiently flexible to allow a high degree of bending as compared with the first section. A critical feature of the present invention is that the highly flexible second section of the tubular member includes an internal tubular wall portion which has been substantially modified. The internal wall portion can be modified in a variety of different manners in order to obtain the object of reducing the potential for jamming, sticking or locking the distal end of some other portion of the guidewire against the internal tubular wall portion.

In accordance with one embodiment of the invention, the internal tubular wall portion is constructed (i.e., physically structured) in a manner so as to deflect the distal end of the guidewire from applying significant forces in a direction normal to the surface of the internal tubular wall. This construction could be in the form of providing a braided sleeve or coil-like structure which wraps around the internal tubular wall. Other constructions might include regular and irregular shapes such as undulations formed in a serpentine pattern on the surface of the internal tubular wall. The coils or configuration of the braided sleeve are constructed so that when the guidewire contacts these constructions, the guidewire is deflected so that the guidewire does not provide substantial forces normal to the surface of the internal tubular wall and therefore does not become jammed or locked into a position on the surface of the internal tubular wall (especially when the second section is bent at an angle of 90° or more).

In a second embodiment of the invention, the internal tubular wall is comprised of materials which minimize the frictional resistance between the internal tubular wall and the distal end portion of the guidewire. Examples of such materials include graphite and Teflon-like materials (i.e., tetrafluoroethylene and fluorocarbon polymers, fluorinated ethylene-propylene resins and other similar non-stick, anti-friction coating compounds) which provide a low coefficient of friction.

In a third embodiment of the invention, yet another tubular member is provided which is positioned within the elongated tubular member and may internally extend from the first section, but at least extends partly within the second tubular section and provides structural (i.e., deflecting normal forces) or material (i.e., anti-friction) features of the types described above which prevent the jamming, sticking or locking of the distal end of the guidewire against the internal tubular wall portion of the second section. The elongated internal tubular member may be movable so as to physically free a jammed end or portion of the guidewire.

A primary object of the invention is to provide a catheter comprised of a guidewire and an elongated tubular member wherein a more flexible section of the tubular member includes an internal wall surface which is constructed and/or comprised of materials so as to aid in preventing the distal end of the guidewire from jamming or locking against its surface.

A feature of the present invention is that the catheter includes a tubular member with a highly flexible section which includes an internal wall member having physical constructural features and/or anti-friction material capable of deflecting the guidewire from applying significant forces in a direction normal to the internal surface of the tubular wall and thus avoid jamming of the wire against the internal wall.

An advantage of the present invention is that the catheter can be used to enter highly curved areas with substantially reduced problems with respect to the jamming of the distal end of the guidewire against the internal tubular surface of the tubular member.

These and other objects, advantages and features of the present invention will become apparent to those persons skilled in the art upon reading the details of the construction, composition and usage as more fully set forth below, reference being made to the accompanying drawings forming a part hereof.

BRIEF DESCRIPTION OF THE DRAWINGS

This invention may be better understood and its numerous objects, advantages and features will become apparent to those skilled in the art by reference to the accompanying drawings as follows.

DETAILED DESCRIPTION OF THE INVENTION

Before the present catheter, catheter device and process for using such is described, it is to be understood that this invention is not limited to the particular catheter devices, components, constructions and materials specifically recited as such may, of course, vary. It is to be understood that the terminology used herein is for purposes of describing particular embodiments only, and is not intended to be limiting since the scope of the present invention will be limited only by the appended claims.

It must be noted that as used in the specification and claims, the singular forms "a", "an" and "the" include plural referents unless the context clearly dictates otherwise. Thus, for example, reference to "a coiled construction" includes a plurality of such constructions, reference to "an anti-friction material" includes a plurality of such materials and reference to "the bending" includes reference to a plurality of bends made by the catheter and/or guidewire and so forth.

Figure 1:
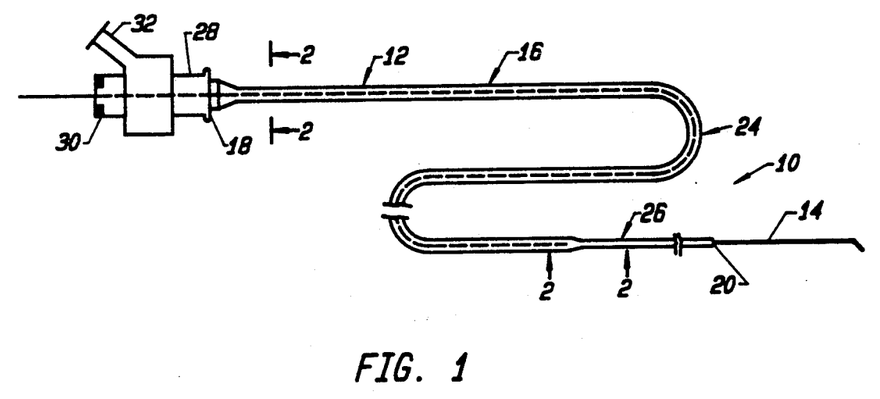
FIG. 1 shows a catheter device, including a catheter constructed according to the present invention.

FIG. 1 shows a catheter device 10 constructed according to the present invention. The device includes a catheter 12 in the form of an elongated tubular member which will be described below, and a guidewire, here indicated at 14. The catheter device is designed for accessing a target site which can be reached only along a small tunnel-like tortuous path within a target tissue, as will be described with reference to FIGS. 11 and 12 below.

With continued reference to FIG. 1, the catheter 12 includes an elongate outer tubular surface 16 having proximal end 18 connected at a fitting and a distal end. The tubular member 12 can be between about 50–300 cm in length, and is typically and more preferably between about 100–200 cm in length. The hollow cylindrical area inside the tube 12 or inner lumen 22 (FIG. 2) extending between the two ends has a preferred diameter of less than about 40 mil, and preferably between about 12–30 mil. One mil is one thousandth of an inch, i.e., 0.001 inch. In one embodiment, the diameter of the inner lumen is between about 2–7 mils greater than that of the diameter of the guidewire 14 carried within the catheter 12. The lumen 22 may have a substantially uniform cross-sectional area along its length, or may vary along the catheter length, for example, the distal end may taper toward a small diameter in a direction away from the proximal end.

As will be described in greater detail below, the catheter or tubular member 12 includes a relatively stiff proximal segment or segment means 24 (a first section) terminating proximally at end 18, and a relatively more flexible distal segment or segment means 26 (a second section) terminating distally at end 20. Thus the first segment or proximal segment 24 has greater structural integrity, a greater resistance to bending, and is more stiff than the second or distal segment 26 which has less structural integrity, greater flexibility, and less resistance to bending than the first section. Although either segment can be comprised of a variety of materials it is important that the materials be modified and/or structured so as to obtain the desired differential with respect to the flexibility of the two sections. The greater stiffness and less flexibility of the first section 24 relative to the softer or more flexible material of the second segment 26 can be measured quantitatively by the bending forces necessary to bend either segment through an equivalent angle. The distal segment is at least about 5 cm long, typically between about 5 cm in length, with the proximal segment providing the remainder of the length of the catheter tubular member. Typically, the proximal segment makes up between about 70%–90% of the total length of the tubular member, and the relatively flexible distal segment makes up the remaining 10%–30% of the length.

Throughout this disclosure, the first or proximal section of the catheter will be referred to as stiffer or less flexible than the second or distal section of the catheter which will be referred to as more flexible and bendable than the first or proximal section. The degree of stiffness, flexibility and/or bendability can be measured quantitatively using tests known to those skilled in the art such as the American Society for the Standard of Testing of Materials (hereinafter referred to as ASTM). In connection with the present invention, the materials used in the catheter were tested using ASTM D747. It should be pointed out that ASTM D747 is generally used in connection with the testing of rectangular pieces of material. Since the present invention is in the form of a tubular catheter, the D747 test was modified for use in connection with the testing of tubular pieces of material. For purposes of this disclosure the ASTM test designated a D747 is incorporated herein by reference for purposes of disclosing methods of testing material with respect to their flexibility.

The above referred-to ASTM D747 modified test was carried out in connection with sections of tubular material to be used for the first or proximal section of the catheter device. The proximal or first section tested under modified D747 testing procedures should give a result of 15,000 psi or more. Results as high as 60,000 psi or more are possible. However, it is more likely that the results will yield a reading of about 40,000 psi or more and are most preferably in the range of about 25 to 35,000 psi with one particular embodiment providing a result of 29,000 psi.

Tubular segments of material to be used in connection with the second section or distal section of the catheter were also tested using the ASTM modified D747 testing procedure. These more flexible or bendable segments gave a reading of 10,000 psi or less and are generally in the range of about 7,000 to 3,000 psi. Although some particularly flexible tubings may have readings below 3,000, e.g., about 1,000 psi, a particularly preferred material has a reading of about 5,500 psi.

Based on the above information, it can be seen that the most flexible D747 reading for the stiffer material (about 15,000 psi) is substantially greater than the least flexible material to be used in connection with the more flexible distal end (about 10,000 psi or less). In general, the modified D747 test reading for the stiffer or proximal section is at least 50 percent greater than the reading for the more flexible or distal segment, and is more preferably more than 100 percent greater. When given in terms of ranges, it can be pointed out that the stiffer or proximal segment is in the range of 2 to 30 times the D747 reading of the more flexible section and more preferably in the range of about 3 to 8 times greater than the D747 reading of the more flexible section.

The inner surface wall of the distal segment 26 of the catheter is constructed such that or comprised of a material such as a low-friction coat which allows the guidewire to be moved axially within the catheter through regions of sharp bends or turns. Four general embodiments of the internal surface of the distal segment are described below in Sections A–D.

The catheter device further includes a proximal end fitting 28 through which the guidewire is received, and through which fluid material can be introduced into the catheter lumen. One standard fitting which is suitable has a guidewire 0-ring seal 30 which can be compressed to provide a suitable seal about the guidewire, while still allowing the wire to be rotated (torqued) and advanced or retracted axially within the catheter, during a catheter placement operation. Fluid material can be introduced into the catheter lumen, for example, from a syringe, through port 32.

A. Catheter With Flexible-Sleeve Distal Segment

Figure 2:
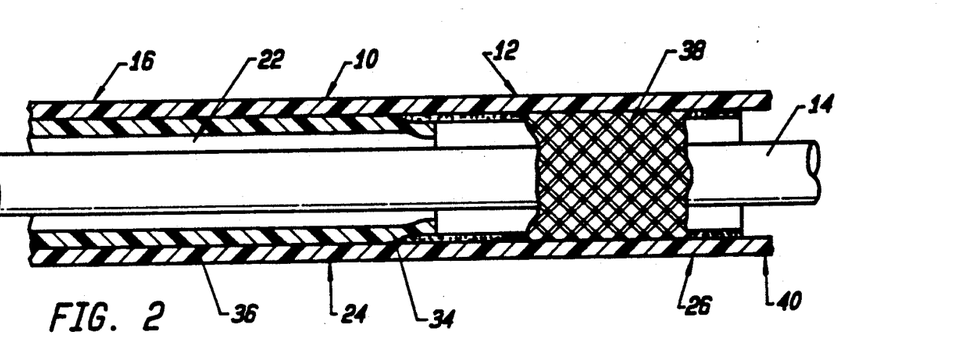
FIG. 2 is an enlarged, sectional view of the catheter, taken along the region 2—2 in FIG. 1, in an embodiment in which the internal tubular surface is a braided sleeve.

FIG. 2 shows an enlarged cross sectional view of a region of catheter 10 in the region of transition between the two segments, indicated at 2—2 in FIG. 1. As seen, proximal segment 24 is composed of inner 34 and outer 36 coaxial tubes which are tight-fitting and/or essentially integral with respect to each other. The stiffness in the proximal segment 24 is provided predominantly by an additional coaxial tube 34. The inner, stiffer tube 34 is preferably polypropylene or high-density polyethylene tubing having a wall thickness of between about 2-4 mils. The outer, more flexible tube is preferably low density polyethylene or silicone tubing, also having a preferred wall thickness of between about 2-4 mils. As defined herein, high- and low-density polyethylene have the usual trade meaning which is applied to the density grade of polyethylenes which are commonly used in extrusion. With respect to the present invention it is not critical that the materials be low and/or high density polyethylenes or silicon material. Any materials having differing properties of the type described above can be used to make up the two different tubular members. What is important is that the outer tube be comprised of a material of less flexibility and structural integrity and greater flexibility relative to the inner tube which is comprised of a material of greater structural integrity and stiffness and less ability to bend relative to the outer tube. By comprising the tubes of the different types of materials it is possible to include the first segment which is stiffer and less bendable and the second segment which is flexible and more easily bendable relative to the first segment.

It will be recognized that other tubing materials whose wall thickness can be adjusted to give comparable tubing flexibilities will be suitable, with the constraint that the total wall thickness of the proximal segment should be less than about 10 mils, and that the number of tubing layers of constant or varying flexibility forming the segments, or portions thereof, can be varied to achieve desired flexibility properties in the tube. As an example, the proximal and distal segments may each be formed as a single layer tube, and joined together at the interface by suitable chemical adhesion and/or by overlapping the two tubes in a short interface region.

In the specific embodiment shown in FIG. 2, the low-friction surface coat in the catheter is provided by a flexible braided sleeve 38 formed by braid-weaving relatively hard filament material, such as metal, nylon, or filaments of Teflon-like materials. The sleeve may be made by conventional braid-weaving methods, such as described in U.S. Pat. No. 4,870,887 (incorporated herein by reference to disclosed such brands and their method of production), where the density and radial pitch of the braid may be varied according to the weave conditions.

In one preferred embodiment, the filaments used in making the sleeve are very fine platinum filaments, and the sleeve is woven under conditions which produce a loose weave having a radial pitch, defined by the angle of the weave with respect to the radial direction in the sleeve, of between about 20°-60°.

The catheter can be constructed, according to one method, by anchoring the proximal end of sleeve 38 between the tubes 34 and 36 forming the proximal segment, as shown in FIG. 2. The outer tube is preferably a heat-shrink material which is placed over the over the sleeve and inner tube and heat shrunk to form a snug fit over both the inner tube and sleeve 38. The sleeve is now anchored at the proximal end and tightly encased along its length by the distal-segment tube.

In the embodiment of the invention shown in FIG. 2, the distal segment includes a distal extension 40 which extends beyond the end of sleeve 38. That is, the second or distal segment 26 includes (a) a proximal region having an inner tubular wall surface in which the frictional coefficient between that surface and the guidewire is significantly reduced, and (b) a region where this wall surface provides higher friction, but is an overall lower-mass tip region whose inertial mass is more closely matched with that of the tapered distal region of the guidewire. The latter feature reduces the tendency of the catheter to force the guidewire out of a bent or curved condition as the catheter is advanced over the distal end region of the guidewire. Explaining further, a relatively low mass at the distal tip region of the catheter may be necessary for tracking the catheter along a tapered region of the guidewire through a sharp bend or turn, even though the reduced catheter mass smaller is gained at the expense of increased friction in this tip region.

Alternatively, the inertial mass in the distal segment of the catheter can be reduced by decreasing the mass of the sleeve, either by employing a lighter or thinner sleeve filament or by reducing the density of filament(s) in the sleeve. It will be appreciated from Sections B–D below that several embodiments of the present invention provide a low-mass surface coating which combines reduced frictional coefficient with very little increase in the mass of the distal segment. The present invention contemplates a distal segment having combined types of low-friction coat, for example, a sleeve coat along a proximal region of the distal segment and one of the lower-mass low-friction coats described in sections B–D along the most distal region of the distal segment.

Figure 3:
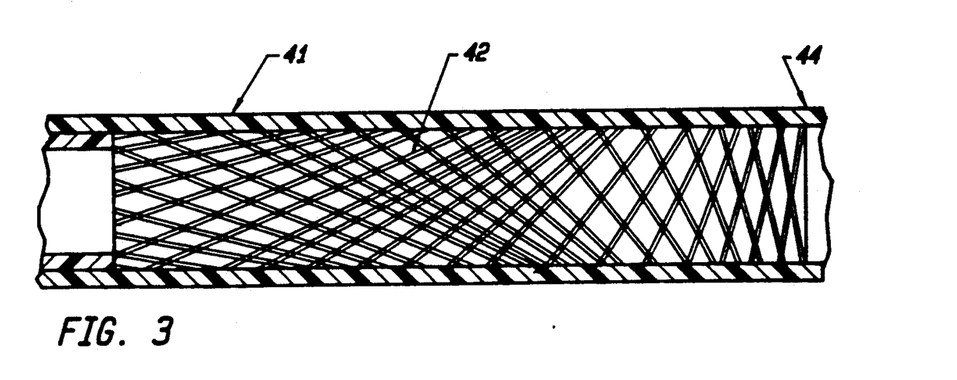
FIG. 3 is a cutaway view of a portion of the distal-end segment of a catheter similar to the one shown in FIG. 2, but where the braided sleeve has a reduced density and increased radial pitch on progressing toward the catheter's distal end.

FIG. 3 shows an alternate embodiment of a sleeve catheter 41, in which the braided sleeve, here indicated at 42, has a continually reduced pitch and weave density in a direction progressing toward the distal tip 44 of the catheter (toward the right in FIG. 3). The sleeve 42 may be formed by conventional braiding methods, where the angle of filaments taken into the braid weave, and the rate of filament taken into the weave, is varied during weaving to obtain the desired change in braid pitch and density. Moving alone the sleeve 42 to the right it can be understood that the sleeve provides greater flexibility, as well as reduced mass, on progressing distally.

In the above-described embodiments, the internal tubular surface of the distal portion of the catheter is provided with structural features in the form of different types of braided sleeves. These structural features aid in preventing the jamming, sticking or locking of the internal surface of the catheter against an external surface of a guidewire. Other structural embodiments are possible. More specifically, the internal surface of the distal portion of the catheter can be constructed to include other structural features different from the braided sleeve which achieves similar results. What is important is that the structural features provide some ability to deflect normal forces which will be applied by the guidewire against the internal tubular surface so as to prevent jamming, sticking or locking of the guidewire against the surface.

Another embodiment of the invention (shown in FIG. 2A) in which the braided sleeve described above is replaced with a wound-filament coil. This embodiment has been described in the above-referenced co-pending patent application Ser. No. 355,500. The coil 38A is preferably formed of a radio-opaque material, such as platinum, and has a pitch of which is preferably between 1.2–2 times the thickness of the filament. The coil 38A may be positioned like the braided sleeve 38 and may be encased in the distal polymer tubing, for example, by heat-shrinking the tube about the coil, as described above.

Figure 2A:
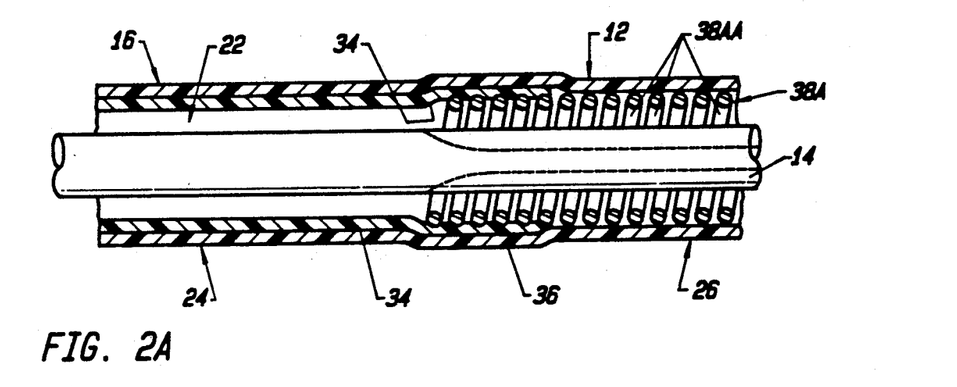
FIG. 2A is the same view as FIG. 2 showing the wire coil in place of the braided sleeve.

The sleeve 38 or 38A may be formed of a radio-opaque filament material, such as platinum, or may be plated or coated with a radio-opaque material, such as gold, for a fluoroscopic viewing.

Both the above-described braided sleeve 42 and the wound-filament coil 38A described within copending application Ser. No. 355,500 provide a structural element which aids in deflecting the distal end or some portion of the distal end of the guidewire from being jammed, stuck or locked against the internal tubular surface. Both the coils and the braided sleeves can be constructed in a variety of different manners in order to obtain the desired results of preventing or alleviating the presentation of substantial forces from the distal portion of the guidewire in a direction normal to the surface of the internal tube. Further, both the coils and the braiding can be constructed of a variety of different materials. It is preferable if the coils and/or braiding are comprised of materials so as to reduce as much as possible the frictional resistance between the internal surface of the tubing and the external surface of the guidewire. Reduced friction aids in preventing the jamming or locking of the distal end or any part of the second section of the guidewire against the internal surface of the tube, that is, against the outer surface of the braiding or coiling component.

B. Discrete-Particle Coating

In a second general embodiment (see FIGS. 4A and 4B), the low-friction surface coat on the distal segment of the catheter is provided by means of a plurality of low-friction particles embedded in or otherwise attached to the inner wall of the distal segment tube 26. An embodiment of the invention in which the coating includes spherical metal particles embedded in the inner wall of the distal-segment tube has been described in the above-referenced co-pending patent application Ser. No. 355,500. Briefly, metal spheres having preferred diameters between about 1–3 mils are embedded in the distal segment 26, e.g., as the tube is being extruded.

Figure 4A:
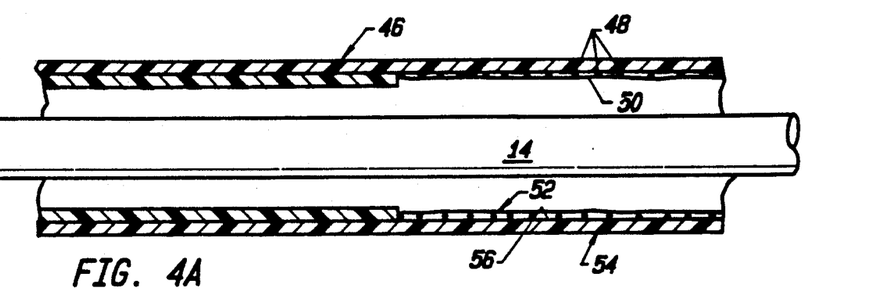
FIGS. 4A and 4B are enlarged sectional views of a catheter constructed according to a second general embodiment, showing a distal-end segment of a catheter having a carbon-particle coating (4B) formed by drying a carbon slurry on the wall of the distal segment (4A)
Figure 4B:
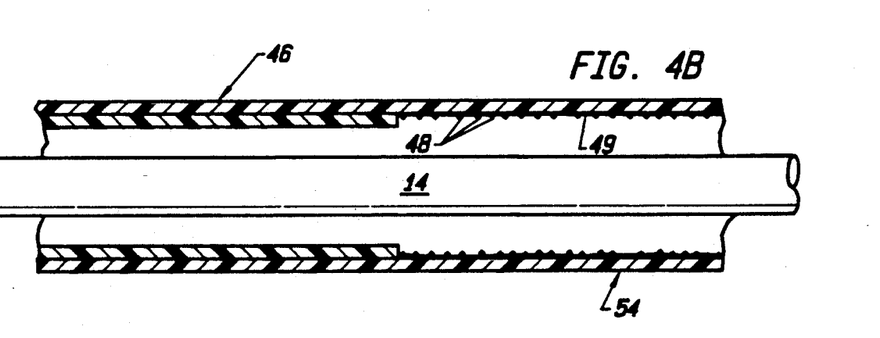

The particles are provided in sufficient number such that the surface density of the particles insures substantially uninterrupted contact between the spheres and a guidewire, when the distal segment is advanced over a looped or sharply bent portion of the guidewire. Preferably the particle density and size is such as to produce sphere-to-sphere contact when the catheter is moved toward a sharply bent configuration. The particle density acts to resist catheter bending beyond the point where the particles are brought into contact with one another, thus serving to prevent kinking in the catheter.

An alternative embodiment of a catheter 46 having a discrete-particle coating is illustrated in FIGS. 4A and 4B. Here the particles 48 are carbon, preferably graphitic, particles which are deposited on the inner wall of the distal segment in a suitable binder. In one preferred method, graphite particles 48, such as particles 48 in FIG. 4A, in the $\frac{1}{2}$–2 mil size range are suspended in a liquid resin mixture 50, such as a mixture of unpolymerized or partially polymerized polyurethane or phenolic resin in the presence of a suitable catalyst, to form a particle slurry 52. The slurry is introduced into a distal catheter segment 54 to coat the inner wall 56, as illustrated in FIG. 4A.

The slurry binder is polymerized under solvent-removal conditions, typically by placing the catheter under vacuum and rotating the segment during solvent removal to maintain an even coat during drying. Plasma treatment technologies can be used. The final binder coat is indicated at 49 in FIG. 4B. Methods for preparing and hardening resin mixtures which can be polymerized at relatively low temperatures are known. The distal-segment tube may be mechanically or chemically abraded prior to coating, to produce improved bonding of the binder layer to the wall of the tube. Alternatively, chemical bonding agents can be incorporated into the binder to bond the polymer in the binder to the segment wall. Such bonding agents are well-known, e.g., as described in U.S. Pat. No. 3,698,931 incorporated herein by reference to disclose such bonding agents.

Alternatively, the carbon particles may be embedded in the inner wall of the distal-segment tube during extrusion, as described above with respect to metal particles.

It will be appreciated that other low-friction particles, such as anti-stick Teflon-like material or nylon beads may be employed in forming the discrete-particles surface coating. An advantage of carbon or polymeric beads over metal beads is their lighter weight, which allows better trackability over the tapered region of the guidewire, for the reasons discussed above. The carbon or polymer-bead particles may be plated with a radio-opaque material, such as gold, for fluoroscopic viewing.

Including the particles on the inner surface of the tubular wall provides structural features which aid in deflecting the distal or second section of the guidewire so as to prevent the guidewire from applying substantial forces normal to the surface of the tubular wall and thus prevent sticking, jamming or locking the distal portion of the guidewire against the inner wall surface. In addition to providing the structural features which deflect the guidewire the particles can be comprised of the above-referred to anti-friction materials which facilitate the movement of the distal end of the guidewire along the inner tubular surface. Thus, like the braided member embodiment described above, the particle coating embodiment described in this section can include both structural features for deflecting the guidewire and composition (i.e., anti-friction material) features for reducing friction, both of which provide the desired result of the invention which is to avoid to the greatest extent possible the jamming, locking or sticking of the guidewire against the inner tubular surface when the tube and guidewire are bent repeatedly while being moved through a tortuous course.

C. Coextruded Polymer Surface Coating

Figure 5:
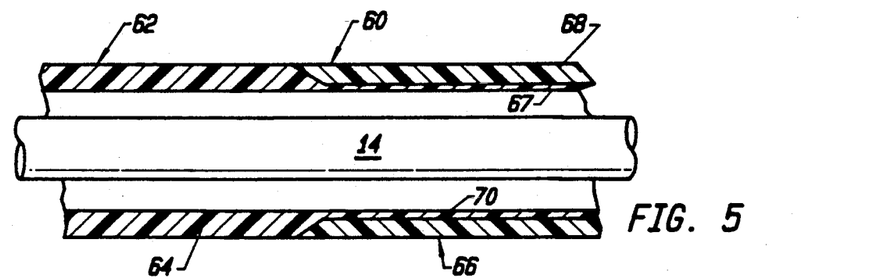
FIG. 5 is an enlarged, sectional view of a catheter constructed according to a third general embodiment, where the distal-end segment includes a thin-walled, relatively stiff inner lining or coat and a thicker-walled, relatively more flexible outer tube.
Figure 6:
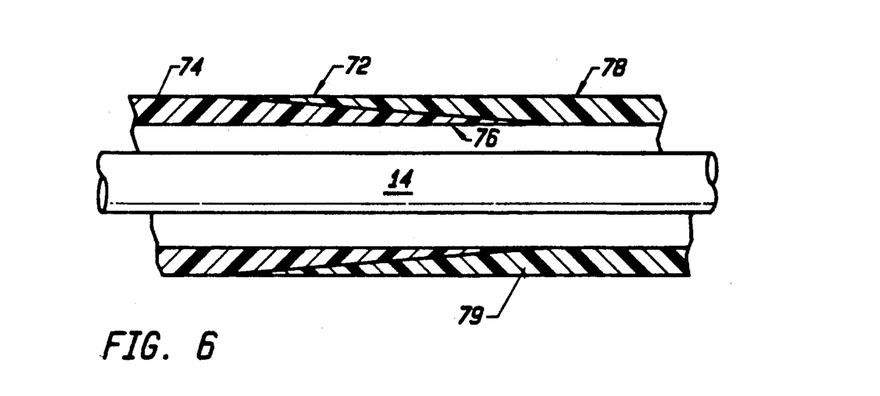
FIG. 6 is a view of a catheter embodiment like that shown in FIG. 5, but where the thickness of the inner tube in the distal-end segment is tapered on progressing toward the distal end of the catheter.

In a third general embodiment, illustrated in FIGS. 5 and 6, the low-friction surface coating in the distal segment of the catheter is provided by a relatively hard-surfaced polymer tube. One catheter having this general construction is shown at 60 in FIG. 5. As in the earlier-described embodiments, the catheter includes a first or proximal segment 62 formed of a relatively stiff, non-deformable polymer tube 64, such as high-density polyethylene, polyurethane, polypropylene, or Teflon-like material as described above, and a distal segment 66 formed of an outer, relatively flexible, deformable polymer tube 68, and an inner distal extension of tube 64.

As seen, tube 64 is sharply reduced in wall thickness at the transition zone between the two segments, yielding a thin-walled tube section 70 which forms the inner surface 67 of segment 66. Typically, the wall thickness of the inner tube is between about 0.5–1 mil, and about 10–20% of the wall thickness of the outer tube 68. The surface 67 can include structural features or be comprised of materials which together or alone prevent jamming of the guidewire 14.

The catheter can be formed by coextrusion, according to known tube co-extrusion methods, such as detailed in U.S. Pat. Nos. 4,680,156 and 4,499,041, each of which are incorporated herein by reference to disclose such methods. The extrusion conditions are adjusted to extrude (a) a single-layer section of relatively rigid polymer tube within a more flexible outer tube, (b) in a transition zone in which the wall-thickness of the inner tube is reduced, and (c) a distal segment in which the inner tube has a fixed, reduced wall thickness.

Alternatively, the catheter may be constructed by first forming the single proximal tube with the reduced-thickness distal extension, then covering the distal extension with a relatively flexible distal tube. The proximal tube and its thin-walled extension can be formed, according to one method, by extrusion processing known to those skilled in the art, or by thinning an end section of the extruded tube by heating an stretching the end portion. In still another approach, a constant-thickness proximal tube is machined in its distal region to form the thin-walled portion.

The outer, more flexible tube in the distal section can be formed over reduced-thickness inner tube section by heat-shrinking the outer tube over the inner one, by binding the two tubes, or by coating the inner tube with a flexible-polymer outer coating, such as by conventional dipping or spraying methods. FIG. 6 illustrates a catheter 72 in which the proximal tube, indicated at 74, has a gradual taper in a proximal region 76 of a distal segment 78. The outer, more flexible tube, shown at 79 has a corresponding taper which preserves the thickness of the wall through the region. The catheter may be constructed by coextrusion, or by one of the alternative methods of covering the tapered, reduced-thickness portion of the proximal tube, with a flexible tube, as described above. An advantage of this embodiment over the catheter shown in FIG. 5 is a reduced tendency of the catheter to kink in the transition region. Also the construction provides greater column strength and torqueability in a region of the distal segment where sharp bends and turns are less likely to be encountered than at the tip region of the catheter.

D. Chemically Hardened Surface Coating

Figure 7:
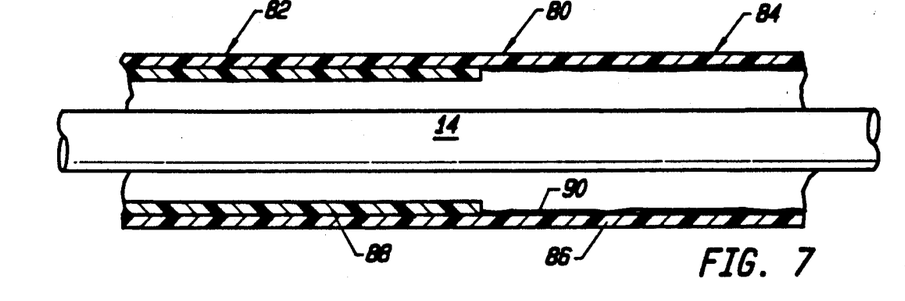
FIG. 7 is an enlarged sectional view of a catheter device constructed according to a fourth general embodiment, where the distal-end segment has a chemically hardened inner coating.

In a fourth general embodiment of the invention, shown in FIG. 7, the low-friction surface coating in the distal segment of the catheter is produced by chemically hardening the inner wall surface 90 of the distal segment tube 82. One catheter embodying this feature is shown at 80 in FIG. 7, which shows proximal and distal segments 82, 84, respectively, having the general construction described above. Specifically, the distal segment is formed by a distal extension of an outer tube 86 beyond the end of a stiffer, less deformable inner tube 88.

The low-friction surface 90 in the catheter is formed by chemically treating the inner surface of the distal-segment tube with a surface hardening agent, such as a polymer cross-linking agent. For example, a distal-segment tube formed of a polyurethane/acrylate copolymer may be hardened by treatment with polyisocyanate (see PCT Application Serial No. 86/AU27 020486, incorporated herein by reference to disclose such methods of treatment). Alternatively, a hydroxylated polymer distal-segment tube, such as one made of polyvinyl alcohol, may be cross-linked using ethyl silicate (see European Patent Application Serial No. 83/102315). Generally, the depth of cross-linking within the distal-segment tube can be controlled by passing a solution of the cross-linking reagent through the tube as it is extruded, or heated. The degree of hardness may be controlled by techniques which are well-known in the polymer field.

It will be appreciated that the hardened surface coating can also be achieved by coating the wall surface with a hard-surface coating, such as a metal, polymer, or graphitic coating, applied by known sputtering, plating or coating techniques.

The low-friction surface or coat 90 may be constructed in a variety of different configurations. However, it is most preferable to keep the surface 90 with a highly glossed or smooth configuration in order to take maximum advantage of the anti-friction coating. By providing the hardened, highly glossed, smooth surface 90 it is possible to obtain the essential object of the invention which is to reduce any sticking or jamming of the distal end of the guidewire against the surface 90 when the guidewire and tubular catheter must be moved relative to each other and both are in a sharply bent configuration. The distal end of the guidewire should be comprised of a material which takes into consideration the composition of the surface 90. Clearly, the two materials, that is the material making up the surface 90 and the material making up the surface of the distal end of the guidewire, should be such as to avoid sticking——that is avoid any friction between the two surfaces and thus provide the lowest possible coefficient of friction when these two surfaces are forced against each other and move across each other.

E. Guidewire Construction

Figure 8:
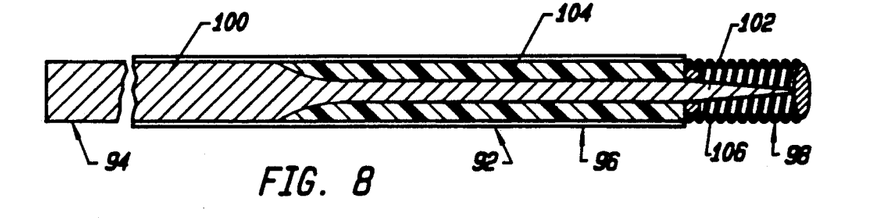
FIG. 8 illustrates an enlarged, fragmentary sectional view of one preferred type of guidewire for use in the catheter of the invention.

FIG. 8 shows one preferred type of a guidewire 92 which can be used in a catheter device of the present invention. Guidewires and their construction have been described in detail in U.S. Pat. No. 4,832,047 which is incorporated herein by reference to disclose such. Briefly, the guidewire includes a flexible proximal section 94 having a typical length between about 40–250 cm, an intermediate section 96 having a length between about 15–60 mils, and a most flexible (relative to the other sections) distal end section 98 whose length is between about 1–10 cm. The core 100 and 102 is tapered from the proximal-section diameter 100 down to a reduced diameter 102 which is preferably about 4–20 mils and between about 10%–50% of the core's proximal segment diameter.

Two segments 100 and 102 making up the core of the intermediate section of the wire are covered along their length by a flexible polymer covering 104, which functions to provide a smooth outer surface of the intermediate section, and to increase the column strength of the reduced-diameter core in the intermediate section. Covering 104 is preferably formed of a polymer, such as Teflon-like material, polyolefin, or polyurethane which can be bonded or otherwise tightly affixed to the core wire.

The distal section portion of the core is fully or partially encased in a flexible sleeve 106. The sleeve shown in FIG. 8 is a soft, flexible helical coil which is formed conventionally, e.g., as described above. It is noted that the portion of the guidewire over which the flexible distal segment of the catheter is advanced is predominantly the smooth-walled proximal section, rather than the coil-encased distal wire segment.

The guidewire may be constructed to include a plurality of different types of coatings on its outer surface. For example, the guidewire may be constructed so that the outer surface has structural configurations which aid in preventing the jamming or locking of this outer surface against the inner tubular wall surface of the catheter tube. Further, the outer coating of the guidewire may be comprised of materials which aid in reducing the frictional resistance between the outer surface of the guidewire and the inner tubular surface when these two surfaces are moving relative to each other. The surfaces of the two components, that is the outer surface of the guidewire and the inner tubular wall surface of the catheter, are preferably each constructed with the structural configurations and material compositions of the other in mind so as to obtain the best possible results. More specifically, the structural features and materials used in each component are preferably chosen so as to obtain the least amount of sticking, jamming or locking of the guidewire against the inner tubular surface of the catheter.

I. Test Characteristics

Figures 9, 10:
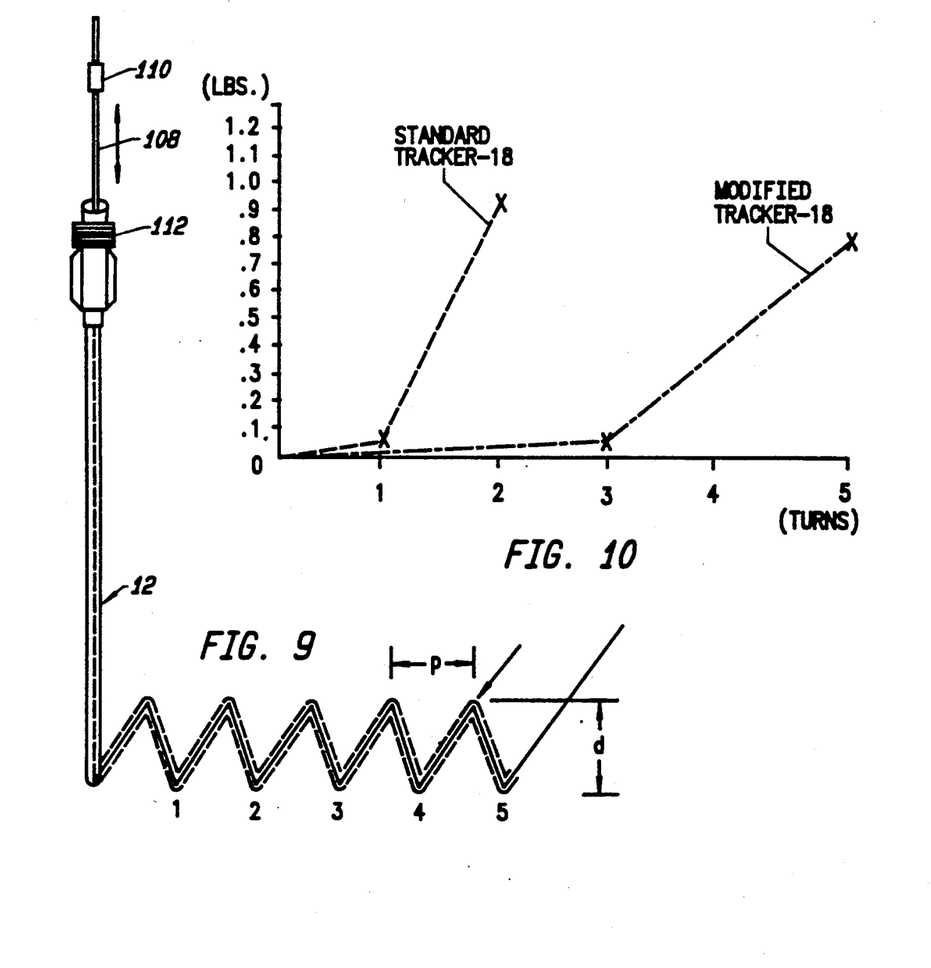
FIG. 9 shows a test configuration for measuring the resistance of a catheter being advanced over a helically-wound wire.
FIG. 10 shows plots of the force required to advance a standard polymer-tube catheter (dashed lines) and a catheter constructed according to the invention (dash-dot lines) over a smooth-surface wire, as a function of the position of the catheter on the FIG. 9 helical wire turns.

The catheter of the present invention is designed for advancement along a guidewire which has been placed, by movement along a tortuous path, in a highly convoluted bent and/or coiled configuration. FIG. 9 illustrates a test configuration for measuring the ability of a catheter of the invention to be advanced along a guidewire containing a series of helical windings.

The guidewire used in this test was a 14-mil stainless steel mandrel 108 having a total length of 175 cm. The proximal end of the mandrel was clamped to the upper jaw 110 of a conventional tensile test device designed to measure the tensile force applied between two jaws 110 and 112, as the jaws are moved relatively toward or away from one another. A distal end portion of the mandrel was formed into a helix 114 having five windings which are numbered 1, 2, 3, 4 and 5 in FIG. 9. The helix diameter d was about 10 mm, and the helix pitch p, about 5 mm.

Each catheter (of the type shown in FIG. 2A) that was tested was flushed with saline and back loaded over the mandrel until the catheter's distal end was just upstream of the coiled portion of the mandrel. The proximal catheter end was locked in jaw 112, as shown, and this jaw was moved downwardly with respect to the stationary jaw 110, to advance the distal segment of the catheter over the coiled portion of the mandrel. The tensile force between the two jaws as this movement occurs was measured conventionally, and the force data were recorded on a chart recorder, along with the position of the catheter's tip on the guidewire coil.

The test catheter was one having a 135 cm proximal segment, a 20 cm flexible distal segment, a lumen diameter of 22 mils, and a 22 mil inner diameter closely wound platinum coil sleeve extending along the entire length of the distal segment. A control catheter had the same construction, but without the distal segment coil sleeve.

FIG. 10 is a graph which plots the force, in pounds, applied between the jaws in the test device, with respect to the position the distal end of the catheter as advanced along the helix. The force curve of the catheter of the present invention is indicated by dash-dot line (the line to the right), and that of the control catheter, by dashed line. The data plotted represents the average of three different test runs for each catheter device.

As seen from FIG. 10, the catheter of the present invention was able to be advanced over three coil windings with very little force (less than about 0.1 lb), with linearly increasing force being required for advance between the third and fifth coil windings. The catheter could be easily advanced over the five-winding helix and only stopped when the proximal segment of the catheter reached the coiled section of the mandrel.

The force curve of the control catheter, shown in dashed lines, indicates the much greater resistance which is encountered in advancing this catheter over a coiled guidewire segment. The catheter could be advanced only over one coil winding at low force, with a sharp increase in force required in advancing along the second winding. The catheter could not be advanced over two complete guidewire windings.

Additional tests carried out in support of the invention show that the guidewire can be advanced easily over a guidewire loop having a loop diameter of 2 mm. By contrast, the smallest loop over which the control catheter could be advanced was a 4 mm diameter loop.

II. Operation

The operation of the catheter and catheter device of the invention, in accessing a target region along a tortuous, small-vessel path will be described now with reference to FIG. 11, which shows a region of soft target tissue 120 such as brain tissue, which includes a portion of a small-vessel, tortuous pathway which must be traversed in reaching a selected target site not shown). The region shown contains vessel 122 which branches into vessel 124, and a vessel 126 which branches from the lower portion of vessel 124. The vessels may have diameters typically between about 2-5 mm or less, and the bends at both of the junctions connecting vessel 122 with the lower portion of vessel 124, and vessel 124 with vessel 126 are greater than 90 degrees.

To reach region 120, the guidewire and catheter, shown at 46, 14, respectively, are first threaded as a unit from an external access site through the vasculature to a region adjacent, but not into the tortuous path region of the target tissue. This is done in the usual case where the catheter must pass through the cardiac aorta by first placing a relatively large-diameter guiding catheter (e.g., about 40 mils inner diameter) from the access site through the aorta and toward the target site. The catheter and guidewire are then threaded through the guiding catheter past the aorta, where large-vessel diameters and high blood flow volumes make it difficult or impossible to control the movement and position of the catheter.

Once the catheter device is beyond the guiding catheter, into the target tissue, the catheter and guidewire are controlled to move toward the target site. Specifically, the guidewire is advanced independently along the tortuous path in the target tissue, according to standard wire manipulations, which include rotating or torquing the wire at each bend, to orient the wire toward the next vessel in the pathway.

Figures 11, 12:
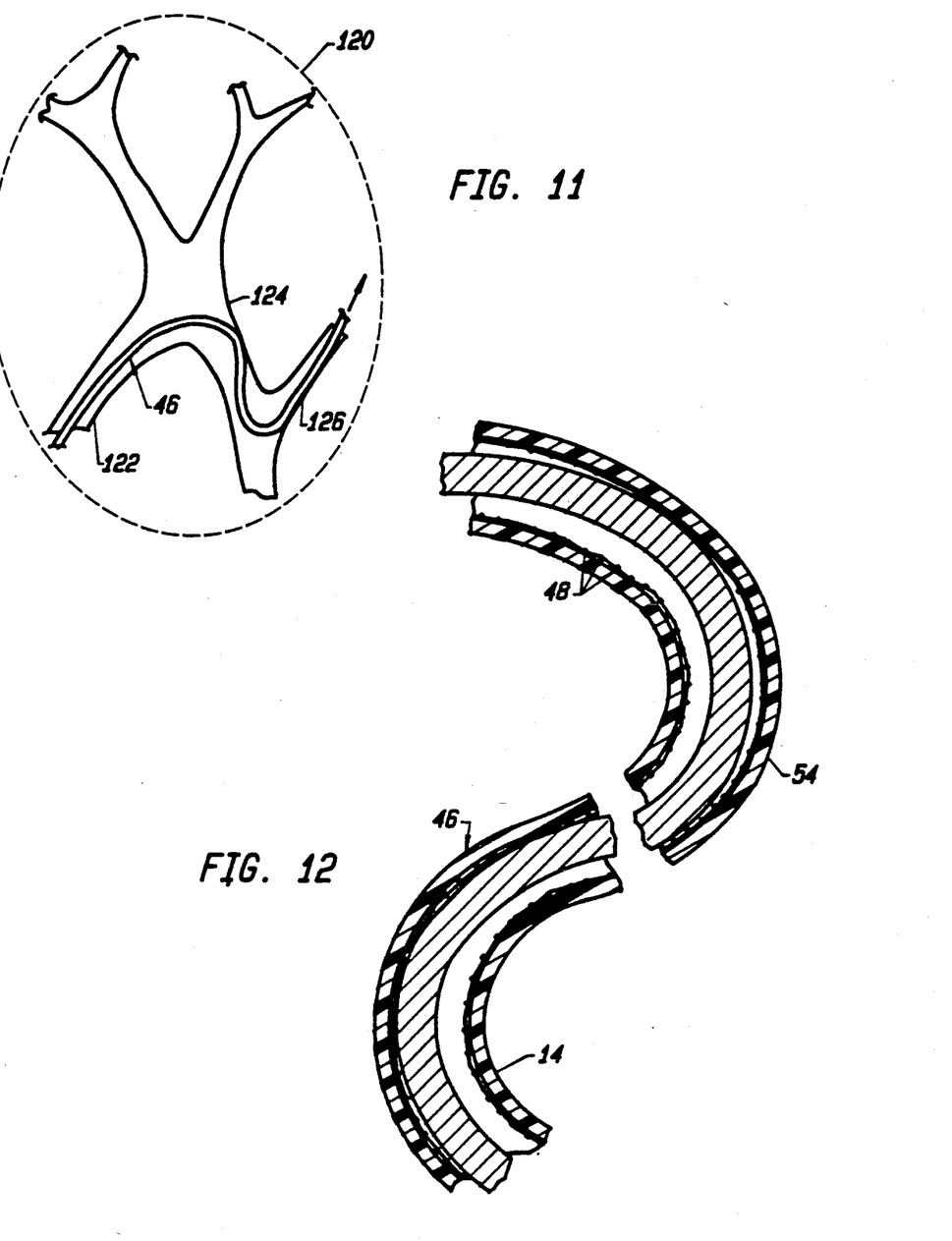
FIG. 11 illustrates a typical small-vessel pathway in which a serpentine configuration like that illustrated in FIG. 11 is encountered.
FIG. 12 is an enlarged cross-sectional view of the catheter of the invention being advanced over a serpentine portion of a guidewire.

For example, in FIG. 11, the wire, when it reaches the junction of vessels 122, 124, is torqued to orient the wire (which has a distal bend) downwardly, and the wire is then advanced with respect to the catheter, into vessel 124. When the next vessel junction is reached, the wire is torqued in the opposite direction, and advanced from vessel 124 into 126. At some point——for example, when the wire has been advanced a total of 2-8 cm ahead of the catheter——the catheter is then advanced over the wire, to thread the catheter up to a point near the distal end of the guidewire.

The bent region of catheter 40 and guidewire 14 in FIG. 11 are shown in enlarged sectional view in FIG. 12. The catheter embodiment shown is that described with respect to FIG. 4B; however, the following discussion applies equally to all of the embodiments described herein). As seen in FIG. 12, the spaced particles on the outer sides of each bend are engaged with the guidewire, as the catheter is advanced over the guidewire, to provide a low-friction contact between the wire and catheter lumen. As detailed above, the reduced friction, due at least in part to the non-deformability of the particles, allows the catheter to be advanced over sharper bends, and with substantially less axial force, than a flexible polymer tube alone.

Once the catheter has been advanced to the target site, the guidewire is withdrawn to allow a fluid material to be injected into the site. The injected material may include: (1) radio-opaque agents for viewing blood vessel anatomy and blood flow characteristics in the target region; (2) vaso-occlusive agents, such as a suspension of collagen fibers which can be used to produce small-artery vaso-occlusion in the tissue region supplied by the target vessel; and (3) pharmacological agents, such as anti-tumor drugs which are effective against identified disease states at the target site.

From the foregoing, it can be appreciated how various objects and features of the invention are met. The novel catheter construction described herein allows for tracking along a tortuous path over a guidewire containing multiple loops or bends whose small radii of curvature, with substantially reduced axial force needed in advancing the wire. This feature allows the catheter access to a variety of deep tissue target sites which have been inaccessible heretofore because of inability to advance the catheter along the guidewire and/or locking of catheter with the guidewire in regions of sharp bends.

In several of the embodiments, the inertial mass contributed by the low-friction surface coating is relatively small, and thus has little effect on the ability of the catheter to track the guidewire over sharp bends or turns in the tapered region of the guidewire.

Where the flexible surface structure is a radio-opaque material, such as gold, platinum, or tungsten wire, the distal segment of the catheter can be readily visualized fluoroscopically, allowing the user to view the extent of catheter advance over a guidewire and thereby better control the catheter placement operation. Alternatively, the distal-segment tube can be provided with radio-opaque banding or embedded radio-opaque material to allow fluoroscopic viewing of the distal segment during use.

The catheter can be easily manufactured using conventional catheter production methods, including coil winding and polymer tube extrusion methods.

While the catheter and catheter device have each been described with reference to specific embodiments thereof, it should be understood by those skilled in the art that various changes may be made and equivalence may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A catheter device, comprising:
an elongated guidewire having a proximal and a distal end; and
an elongated polymeric tubular member having an internal diameter of no greater than about 40 mils through which internal diameter the guidewire is positioned, the tubular member being comprised of a first section towards a proximal end of the tubular member, which first section has an internal tubular wall portion of a first material, has substantially less flexibility relative to a second section at least 5 cm long which is positioned toward a distal end of the tubular member, the second section being sufficiently flexible to allow a high degree of bending as compared to the degree of bending possible with the first section, the second section of the tubular member having a braided sleeve internal tubular wall portion which braided sleeve comprises a material different from and that is more lubricious than the internal wall surface of the first material and further is constructed so as to deflect the distal end of the guidewire in axial direction of the second segment of the tubular member.

2. The catheter device as claimed in claim 1, wherein the internal tubular wall portion is comprised of a material capable of minimizing frictional resistance between the surface of the internal tubular wall and the surface of the distal end of the guidewire.

3. The catheter device as claimed in claim 1, wherein the braided sleeve is comprised of an anti-friction material.

4. A catheter for use in combination with a guidewire for accessing a target site in an internal body tissue, from an external body site to the internal body tissue, and along a tortuous, small-vessel pathway within the tissue, said catheter comprising:
an elongated polymeric tubular member having proximal and distal ends, and an inner lumen extending between these ends, the lumen having a diameter which is no greater than about 40 mils, said member including a proximal segment and a distal segment at least about 5 cm long which is adapted for tracking the wire along such tortuous path, the distal segment being more flexible than the proximal segment;
said distal segment being composed of a polymer distal-segment tube, and an internal surface comprising a braided filament sleeve carried on the inner surface of the distal-segment tube, for providing substantially uninterrupted reduced-friction contact with a guidewire, as the distal segment of the catheter is advanced over a looped or bent region of the guidewire, the internal surface means being less deformable and flexible than the distal segment tube.

5. The catheter of claim 4, wherein said polymer distal-segment tube is composed of low-density polyethylene.

6. The catheter as claimed in claim 4, wherein the braided-filament and film is comprised of an anti-friction material.

7. The catheter of claim 4, wherein said filaments forming said braided sleeve are composed of material selected from the group of elements consisting of: platinum, acrylic, nylon, and Kevlar.

8. The catheter of claim 4, wherein the braid of the braided-filament sleeve has a pitch, said pitch being reduced in a direction progressing toward the distal end of the catheter to achieve a greater flexibility in the distal catheter end.

9. The catheter of claim 4, wherein said distal-segment tube further includes a distal extension composed of a polymer tube that is more flexible and deformable than the inner surface means.

10. A catheter device for accessing a target site in an internal body tissue along a tortuous small-vessel pathway within the tissue, said device comprising:
a guidewire having a proximal end, an intermediate region, and a distal end, and a wire diameter of no greater than about 10 mils; where the distal end region is encased in a wire coil, and the intermediate region is smooth-walled adjacent the distal end region and is in contact with the catheter distal segment means during a catheter placement operation and
a catheter comprising an elongate polymeric tubular member having proximal and distal ends, and an inner lumen extending between these ends, with a diameter which is no greater than about 40 mils, said member including a proximal segment and a distal segment at least about 5 cm long which is adapted for tracking the wire along such tortuous path, said distal segment being more flexible than the proximal segment, said distal segment being composed of a polymer distal-segment tube, and surface means carried on the inner surface of the distal-segment tube, for providing substantially uninterrupted reduced-friction contact with a guidewire, as the distal segment of the catheter is advanced over a looped or bent region of a guidewire the surface means being less deformable and more flexible than the distal-segment tube.

11. The catheter device of claim 10, wherein the distal segment is able to be advanced over a guidewire loop having a 2 mm diameter.

12. A catheter for use in combination with a guidewire for accessing a target site in an internal body tissue, from an external body site to the internal body tissue, and along a tortuous, small-vessel pathway within the tissue, said catheter comprising:
an elongated polymeric tubular member having proximal and distal ends, and an inner lumen extending between these ends, the lumen having a diameter which is no greater than about 40 mils, said member including a proximal segment and a distal segment at least about 5 cm long which is adapted for tracking the wire along such tortuous path, the distal segment being more flexible than the proximal segment;
said distal segment being composed of a polymer distal-segment tube, and an internal surface means including an array of substantially non-deformable smooth-surfaced particles carried on the inner surface of the distal-segment tube, for providing substantially uninterrupted reduced-friction contact with a guidewire, as the distal segment of the catheter is advanced over a looped or bent region of the guidewire, the internal surface means being less deformable and flexible than the distal segment tube.

13. The catheter of claim 12 where the polymer distal segment tube is composed of low-density polyethylene.

14. The catheter of claim 12 where the particles are carbon particles attached to the inner wall of the distal-segment tube by a binder.

15. The catheter of claim 12 where the particles are polymeric beads.

* * * * *